United States Patent
Bzdusek et al.

(10) Patent No.: US 10,603,511 B2
(45) Date of Patent: Mar. 31, 2020

(54) SHAPE BASED INITIALIZATION AND QA OF PROGRESSIVE AUTO-PLANNING

(71) Applicant: KONINKLIJKE PHILIPS N.V., Eindhoven (NL)

(72) Inventors: Karl Antonin Bzdusek, Madison, WI (US); Prashant Kumar, Bangalore (IN); Todd McNutt, Baltimore, MD (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 279 days.

(21) Appl. No.: 15/531,862

(22) PCT Filed: Dec. 3, 2015

(86) PCT No.: PCT/IB2015/059327
§ 371 (c)(1),
(2) Date: May 31, 2017

(87) PCT Pub. No.: WO2016/088075
PCT Pub. Date: Jun. 9, 2016

(65) Prior Publication Data
US 2017/0259082 A1    Sep. 14, 2017

Related U.S. Application Data

(60) Provisional application No. 62/087,264, filed on Dec. 4, 2014.

(51) Int. Cl.
*A61N 5/10*    (2006.01)
*G06F 19/00*   (2018.01)
*G16H 50/20*   (2018.01)

(52) U.S. Cl.
CPC ............ *A61N 5/103* (2013.01); *G06F 19/321* (2013.01); *G06F 19/3481* (2013.01); *G16H 50/20* (2018.01); *A61N 2005/1041* (2013.01)

(58) Field of Classification Search
CPC ........ A61N 5/103–1031; A61N 5/1038–1039; A61N 2005/1041
See application file for complete search history.

(56) References Cited

U.S. PATENT DOCUMENTS 8,180,020 B2   5/2012   Kilby et al.
8,696,538 B2   4/2014   Otto
(Continued)

FOREIGN PATENT DOCUMENTS

WO   2014167461 A1   10/2014

OTHER PUBLICATIONS

Zhang, X. et al., "A methodology for automatic intensity-modulated radiation treatment planning for lung cancer", Physics in Medicine and Biology, 56 (2011) 3873-3893.
(Continued)

*Primary Examiner* — Thaddeus B Cox (57) ABSTRACT

A system and method for automatically generating radiation therapy treatment plans including one or more processors configured to capture geometries of organs at risk and a target volume specific to a subject, and use a shape-based algorithm to mine (152) a knowledgebase (38) of previously constructed treatment plans for similar geometries to the subject. The system and method interfaces (154) dosimetric information from a plan with a similar geometry as a patient specific starting point for a progressive tuning optimization algorithm resulting in fewer iterations. The progressive tuning algorithm (156, 158, 162) generates an optimized treatment plan. The optimized plan is evaluated against treatment goals. Trade-off plans are generated (164) create alternative plans according to unmet treatment goals.

15 Claims, 3 Drawing Sheets

(56) References Cited

U.S. PATENT DOCUMENTS

| | | | |
|---|---|---|---|
| 8,986,186 | B2 | 3/2015 | Zhang |
| 2006/0293583 | A1 | 12/2006 | Saracen et al. |
| 2011/0153547 | A1 | 6/2011 | McNutt et al. |
| 2013/0077752 | A1 | 3/2013 | Zankowski |
| 2013/0085343 | A1 | 4/2013 | Toimela |
| 2013/0268547 | A1 | 10/2013 | Boroczky et al. |
| 2013/0272593 | A1* | 10/2013 | Lee ............ A61N 5/103 382/131 |
| 2013/0289332 | A1 | 10/2013 | Purdie et al. |
| 2014/0378736 | A1* | 12/2014 | Fox ............ A61N 5/103 600/1 |
| 2015/0141733 | A1 | 5/2015 | Kumar et al. |

OTHER PUBLICATIONS

Rosen, I., et al., "Interactively exploring optimized treatment plans". Int J Radiat Oncol Biol Phy 2005; 61: 570-82.

Gopal, R., et al., "Plan space: Representation of treatment plans in multidimensional space", Int J Radiat Oncol Biol Phy 2002; 53: 1328-36.

Zhang, X. et al., "A sensitivity-guided algorithm for automated determination of IMRT objective function parameters", Med Phys 2006; 33: 2935-44.

Zhang, H.H. et al., "Modeling plan-related clinical complications using machine learning tools in a Multiplan IMRT framework." Int J Radiat Oncol Biol Phys 2009; 74: 1617-26.

Wu, B., et al., "Data-driven approach to generating achievable dose-volume histogram objectives in intensity modulated radiation therapy treatment planning", Int J Radiat Oncol Biol Phy 2011; 79: 1241-7.

Craft, D.L. et al., "Improved planning time and plan quality through multicriteria optimization for intensity-modulated radiotherapy", Int J Radiat Oncol Biol Phys 2011.

Wu, B. et al., "Patient geometry-driven information retrieval for IMRT treatment plan quality control", Med Phys 2009; 36: 5497-505.

Petit, S. et al., "Increased organ sparing using shape-based treatment plan optimization for intensity modulated radiation therapy of pancreatic adenocarcinoma", Radiother Oncol 2011; Article in press.

Wu, B. et al., "Using overlap volume histogram and intensity modulated radiation therapy plan data to guide and automate volumetric modulated arc therapy treatment planning: a head and neck case study", Int J Radiat Oncol Biol Phys 2012; Article in press.

Moore, K. et al., "Quantitative Metrics for Assessing Plan Quality", Semin Radiat Oncol 2012 22:62-69.

* cited by examiner

SHAPE BASED INITIALIZATION AND QA OF PROGRESSIVE AUTO-PLANNING

Cross-Reference to Prior Applications

This application is the U.S. National Phase application under 35 U.S.C. §371 of International Application Serial No, PCT/IB2015/059327, filed on Dec. 3, 2015, which claims the benefit of U.S. application Ser. No. 62/087,264, filed on Dec. 4, 2014. These applications are hereby incorporated by reference herein.

FIELD

The present application relates generally to radiation therapy. It finds particular application in conjunction with radiation therapy planning and will be described with particular reference thereto. However, it is to be understood that it also finds application in other usage scenarios and is not necessarily limited to the aforementioned application.

BACKGROUND

In radiation therapy planning, creating a patient specific treatment plan can be a time consuming and tedious task. Many of the steps are redundant and vary little from patient to patient or plan to plan. Many of these steps can be automated using macro languages or scripts, but certain aspects are difficult without tools for writing logical expressions, loops, and other common programming functionality.

In the past decade, technological advancements have provided a big leap in the field of intensity modulated radiation therapy (IMRT), intensity modulated proton therapy (IMPT) and the like, to improve dose delivery. One area that is difficult to automate in current treatment planning is intensity-modulated radiation therapy (IMRT) or volumetric-modulated arc therapy (VMAT) optimization. Recently the research interest has shifted towards methods of automating various tasks involved in plan generation, starting from beam placement to dose optimization, to assist and reduce the workload burden on the clinical user. Optimization is an iterative process where a user attempts to specify planning goals in the form of dose or biological objectives to create an ideal dose to target structures, typically a uniform high dose, and minimize the dose to critical structures.

Plan evaluation is classified into three phases: 1. Physical evaluation, 2. Technical evaluation and 3. Clinical evaluation. The physical and technical aspects of a plan are generally examined by a technician after the completion of the plan. The clinical aspects of a plan are investigated by a radiation oncologist. Currently an IMRT plan is evaluated based on five categories that cover the physical, technical and clinical aspects of a plan: 1. Geometric analysis, 2. Dose distribution analysis, 3. Dose Volume Histogram (DVH) analysis, 4. Parametric analysis and 5. Deliverability analysis.

The geometric analysis is performed to evaluate the optimality of beams placement. Beam placement is a very important step. The quality of optimization is influenced by the number of beams and their angles. Rules have been formulated for optimal beam placement in IMRT in view of increasing the optimality and deliverability of an IMRT plan.

The dose distribution analysis qualitatively verifies the optimality of dose distribution in axial, coronal and saggital planes. This analysis can be further split up into 2D analysis and 3D analysis. 2D dose distribution analysis implies the evaluation of dose distribution slice-by-slice. This type of analysis is used to evaluate the conformality of the prescribed dose with respect to the target volume in each slice. This type of analysis can also reveal the distribution of cold or hot spots in and around the target volume. Cold or hot spots are areas within the target and organs at risk that receive less or greater than the intended dose of radiation. The 3D distribution analysis is useful in determining how conformal a dose distribution is to the overall target volume with respect to a set of beam orientations.

Dose Volume Histograms (DVH) are a powerful tool for evaluating the optimality of a plan. A DVH represents a 3-dimensional dose distribution in a graphical 2-dimensional format. A DVH for target volume graphically represents the quality of the dose distribution in terms of coverage, conformity and homogeneity. The DVH curves for Organs-at-risk (OARs) represent the efficiency at which the OARs are spared in terms of mean and maximum dose.

The parametric analysis is performed to quantitatively verify the optimality of dose. The parameters used in this analysis are: (a) minimum, mean and maximum dose for target volume and OARs and (b) coverage, conformity and homogeneity indices for target volume. Apart from physical metrics for plan evaluation, a plurality of biological metrics are used in plan evaluation. These biological metrics include Equivalent Uniform Dose (EUD), Tumor Control Probability (TCP) and Normal Tissue Complication Probability (NTCP) and the like.

Deliverability analysis is performed in order to evaluate how robust the plan is in terms of dose delivery. This analysis involves the verification of parameters such as number of segments, minimum or average monitor units (MU) per segment, Minimum Segment Area (MSA), total delivery time and the like. MU is a measure of machine output of a linear accelerator in radiation therapy. The deliverability analysis reveals whether or not a plan is realistically deliverable.

Various stages of plan generation have been automated with different techniques. These techniques reduce the burden on the clinical user, i.e. a radiation technician, by automating the plan generation process, such as dose objective manipulation and IMRT/VMAT optimization. Given the complexity involved with radiation therapy treatment plan generation, it is imperative that the user wants a certain amount of manual control and review but at the same time it stops these techniques from being fully automatic. A current auto-planning solution offers one time configuration of user defined template which can be later applied to a new patient for automatically generating a treatment plan.

Specifically, it is difficult to determine the best plan to meet the goals since the definition of best is subjective and variable for the same user from patient to patient. After plan generation, the user weighs various tradeoffs between target goals and organs at risk goals and decides what is acceptable for each patient. Understanding the tradeoffs has been the focus of several technologies. However, one issue with the approaches is that the user has too much more flexibility than needed which makes the workflow too general and less focused for physicians. The present application relates generally to medical imaging. It finds particular application in calibration of a positron emission tomography (PET) detectors, and will be described with particular reference thereto. However, it is to be understood that it also finds application in other usage scenarios and is not necessarily limited to the aforementioned application. The present application combines the shape based method of initializing radiation treatment planning optimization parameters with the progressive tuning of the optimization parameters. It also uses shape based DVH predictions to identify potential trade-offs and provide plan quality QA.

Using shape based methods to determine optimization parameters is limited such that the parameters retrieved are only those used in prior plans (or models) and requires specific knowledge available for the type of treatment desired. The source of the knowledge is not necessarily optimal or driven to the limit. However the shape based method captures trade-offs made in the approved plans and is relatively fast.

Progressive tuning of optimization parameters has the limitation that the initial conditions are the same for each patient and can take significant time to reach the final solution. However, the algorithm strives to drive optimization parameters to the limit.

SUMMARY

Using shape based optimization parameters with progressive tuning will provide a method to capture trade-offs, remove the need to define general optimization goals when there is sufficient knowledge, and drive optimization parameters to the limit all relatively fast. It also provides a mechanism for trade-off plan generation and quality assurance.

In accordance with one embodiment, a therapy planning system for generating an optimal treatment plan, said system comprising at least one processor programmed to: receive a plurality of treatment plan objectives; optimize the plurality of treatment plan parameters based on the plurality of objectives to generate a treatment plan; reformulate the plurality of objectives including at least one of modifying parameters of the plurality of objectives and/or adding one or more additional objectives to the plurality of objectives; and repeat the optimizing based on the reformulated plurality of objectives to generate a reformulated treatment plan.

In accordance with one preferred method of the present application, a method for generating an optimal treatment plan, comprising: receiving a plurality of treatment plan objectives; optimizing the plurality of treatment plan parameters based on the plurality of objectives to generate a treatment plan; reformulating the plurality of objectives including at least one of modifying parameters of the plurality of objectives and/or adding one or more additional objectives to the plurality of objectives; and repeating the optimizing based on the reformulated plurality of objectives to generate a reformulated treatment plan.

In accordance with another embodiment of the present application, a treatment planning system having one or more processors programmed to: determine initial optimization goals by a lookup in a knowledgebase based on the shape relationship between OARs and targets; perform a shape relationship-based algorithm on the current patient's shape relationship and the knowledgebase to find a previously generated plan with a similar shape relationship and retrieve the achieved dose volume histogram; determine optimization goals based on the achieved dose volume histograms; optimize the treatment plan objectives with a progressive algorithm to generate an optimized treatment plan; and compare the optimized treatment plan to treatment plan objectives of previously generated plans in the knowledgebase; and store a final plan in the knowledgebase.

One advantage is streamlined treatment plan analysis for the physician.

A further advantage is that the plan is optimized based on trade-offs captured in the knowledgebase.

Another advantage is that fewer iterations of the progressive algorithms are necessary resulting in increased efficiency.

A further advantage is that IMRT/VMAT planning complexity is reduced.

Another advantage is that deliverable trade-off plans can be easily created that provide alternative plans when the clinical goals were not met by the initial optimized plan.

Still further advantages will be appreciated to those of ordinary skill in the art upon reading and understand the following detailed description.

DETAILED DESCRIPTION OF EMBODIMENTS

Figure 1:
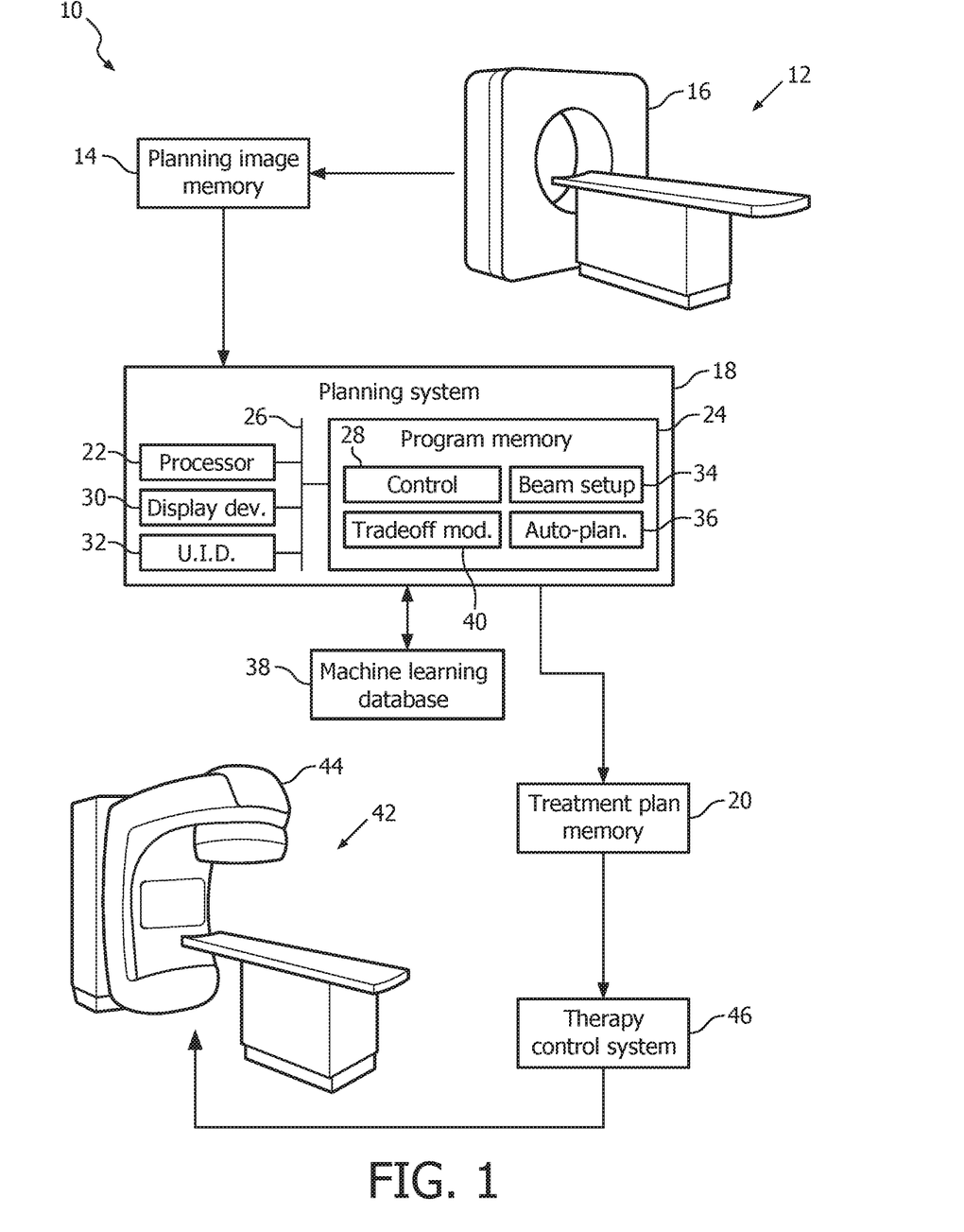
FIG. 1 depicts an IMRT planning system implementing an improved method for automating plan generation.

With reference to FIG. 1, a therapy system 10, such as an intensity-modulated radiation therapy (IMRT) system or a volumetric-modulated arc therapy (VMAT) system, includes an imaging system 12 to generate one or more planning images of a region of interest of a patient. The image volume, i.e. the planning images, is volumetric (i.e., three-dimensional) and typically stored in a planning image memory 14 of the therapy system 10. The region of interest includes one or more target structures and, typically, one or more critical structures or organs at risk (OARs). Each of the target structures is a lesion or other tissue region, such as a tumor, to be irradiated. Each of the critical structures is an organ or other tissue region which is at risk of damage from the radiation intended for the target structures, such as radiation traveling to the target structures, which has passed through the target structures, or which passes closely adjacent the target structures.

The imaging system 12 generates the planning images using one or more imaging modalities, such as computed tomography (CT), positron emission tomography (PET), magnetic resonance (MR), single photon emission computed tomography (SPECT), cone-beam computed tomography (CBCT), and the like. Hence, the imaging system 12 includes one or more scanners 16 corresponding to the imaging modalities, as well as a backend system reconstructing raw image data from the scanners into the planning images. In the illustrated embodiment, the imaging system 12 generates the planning images using, for example, CT and includes a CT scanner 16.

A planning system 18 of the therapy system 10 generates an optimal treatment plan for the patient on the planning images, which are typically received from the planning image memory 14. The optimal treatment plan suitably includes a plurality of treatment fractions, each identifying planning target volumes (PTVs) for the target structures, margins around the target structures, dose profiles for the target structures, dose limits for the critical structures, and therapy beam directions and intensities, and is typically stored in a treatment plan memory 20 of the therapy system 10. The planning system 18 includes at least one processor 22 and at least one program memory 24. The program memory 24 includes processor executable instructions that, when executed by the processor 22, generate the optimal treatment plan. The processor 22 executes the processor executable instructions to generate the optimal treatment plan. The planning system 18 further includes at least one system bus 26 interconnecting the processor 22, the program memory 24, and any other components of the planning system 18.

A control module, computer routine, processor, or the like 28 of the processor executable instructions controls overall operation of the planning system 18, including generation of the optimal treatment plan. The control module 28 suitably displays a graphical user interface (GUI) to a user of the planning system 18 using a display device 30 of the planning system 18. Further, the control module 28 suitably allows the user to interact with the GUI using a user input device 32 of the planning system 18. For example, the user can interact with the GUI to specify parameters, controlling the generation of the optimal treatment plan. In particular, the user specifies regions of interest and organs-at-risk within the image volume located on the planning image memory 14 via the user input device 32 and other unique parameters. In one embodiment, a memory for storing user defined clinical objectives is used. The display device 30 also displays a visual presentation of trade-off values, met and unmet objectives, and specific areas of trade-off.

A therapy beam setup module, computer or software routine, processor, or the like 34 of the processor configures one or more therapy beams used for therapy delivery. This can be performed automatically and/or manually. As to automatic therapy beam setup, an appropriate routine is employed to automatically configure parameters configuring the therapy beam. It is also contemplated that therapy beam setup can be performed using a combination of automatic and manual therapy beam setup. Beam placement is achieved using beam angle optimization or selection methodologies along with the beam configurations followed in standard clinical practice e.g. for head and neck a standard equally spaced 7-9 beam co-planar configurations are typically enough. Additional provision to accept the number of beams input from the user is also possible, in which case the system only optimizes on the beam angles. Iterative adjustment of beam placements is also a possibility if the auto-plan results are not as desired. The automatically configured parameters can then be displayed to the user using the display device 30 and the user can modify the beam parameters, as appropriate, using the user input device 32.

Once the parameters are finalized, an auto-planning module, computer or software routine, processor, or the like 36 generates a candidate treatment plan. The auto-planning module 36 includes receiving input parameters for generation of the treatment parameters. The input parameters include the boundaries of the structures (i.e., the target structures and, typically, the critical structures) within the planning images, as well as therapy beam configuration parameters, which are determined using the therapy beam setup module 34.

The auto-planning module 36 is operatively coupled to a machine learning database 38. The machine learning database 38 is a knowledgebase that stores previously generated radiation therapy plans including target volumes, OARs, patient characteristics, dosimetry information, and the like.

Figure 2:
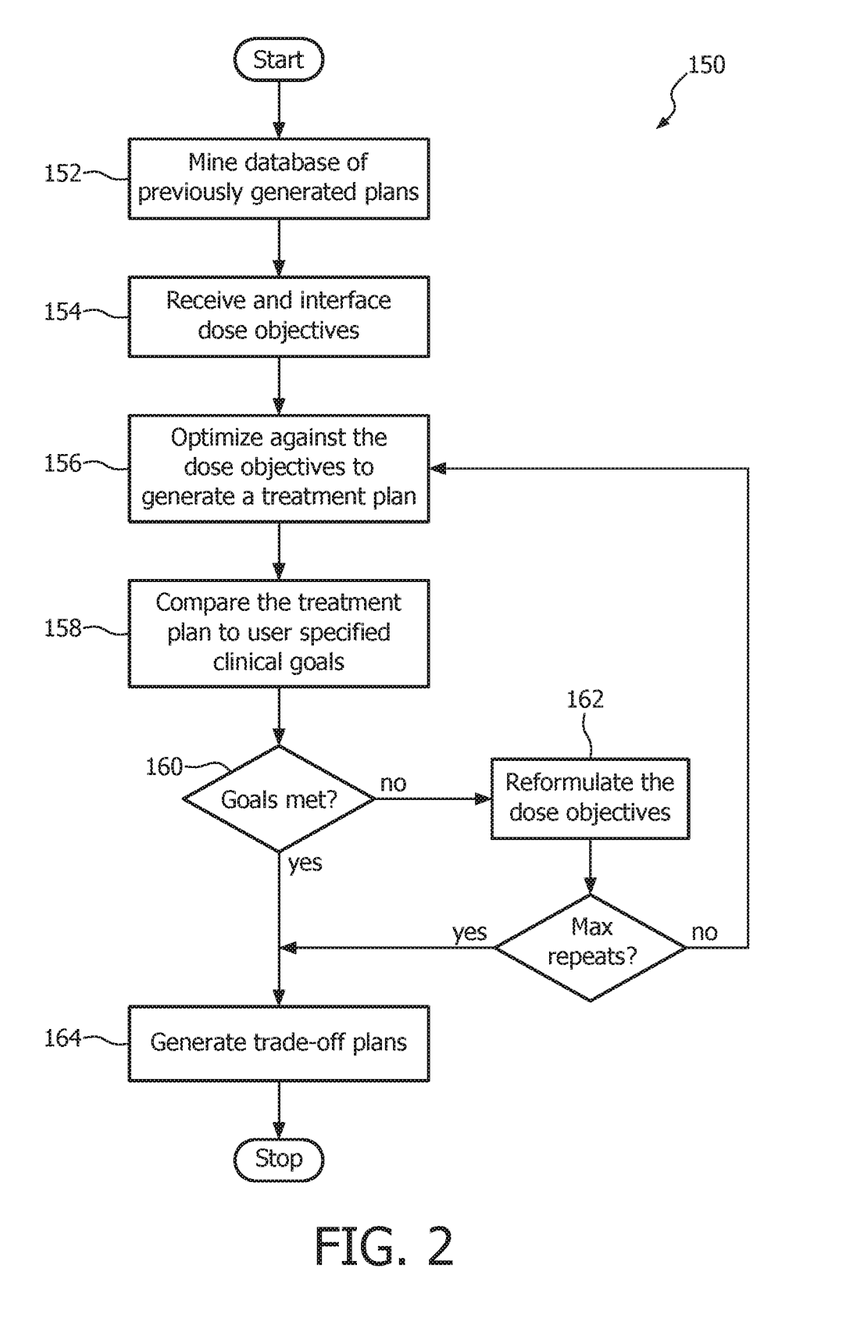
FIG. 2 depicts a method for generating therapy plans.
Figure 3:
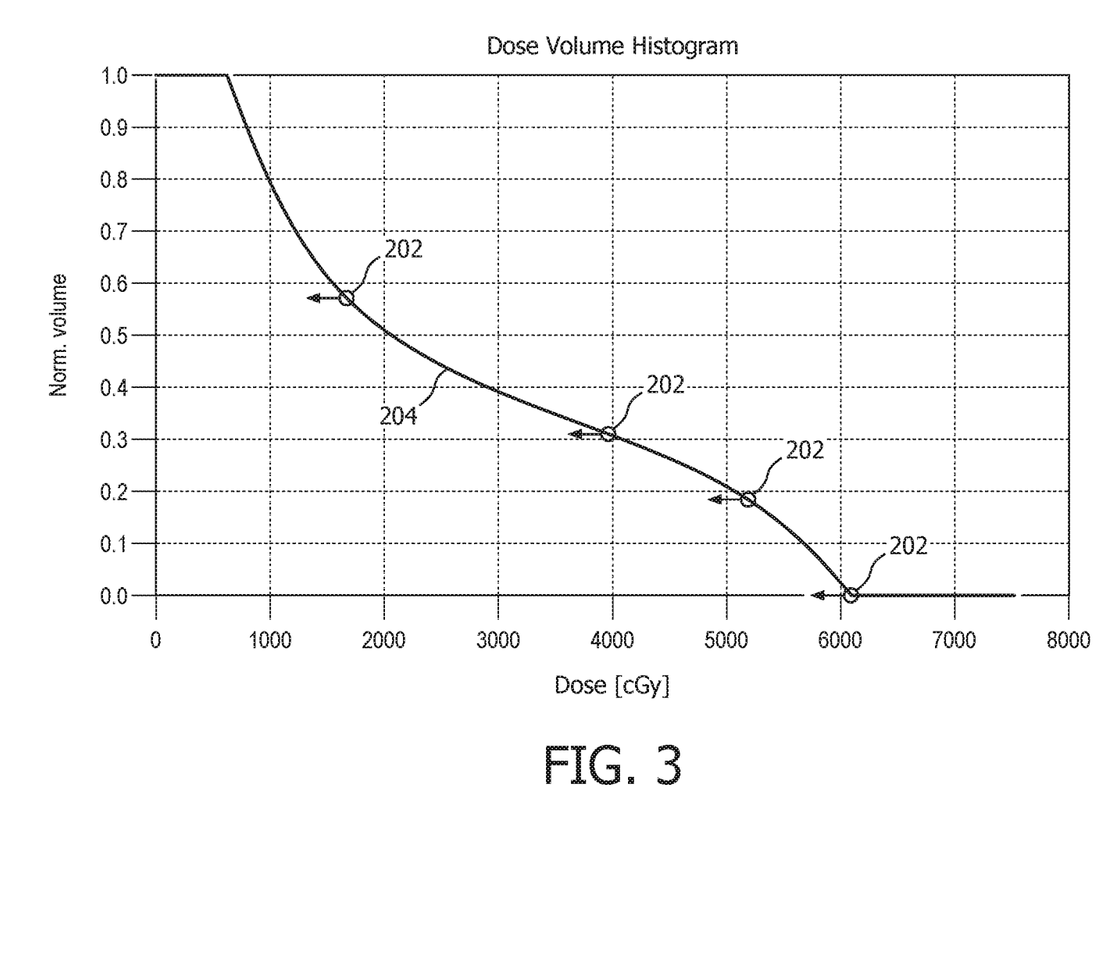
FIG. 3 depicts a DVH curve with inflection point.

With reference to FIG. 2, the auto-planning module 36 uses a shape-based algorithm to capture the shape relationships between the OARs and the target volumes. The shape relationships are used to match plans 152 that have been created for patients with similar geometries. The auto-planning module 36 determines overlaps between target volumes and OARs and characterizes the proximity information into a shape metric such as an overlap volume histogram (OVH). The auto-planning module 36 searches the machine learning database 38 for plans with similar shape metrics. The auto-planning module 36 constructs dose volume histogram (DVH) values 154 from the matched geometries and plans. The DVH values or other dosimetric information related to the OAR is retrieved from the machine learning database 38 of existing plan information and templates. With reference to FIG. 3, the dose volume goals can be derived from inflection points 202 in a DVH curve 204. Other properties of the DVH such as mean dose, equivalent uniform dose (EUD), max dose, and the like can also be used depending on the goals for the OAR. In one embodiment, a different data mining algorithm is used to find similar plans in the machine learning database 38.

The auto-planning module 36 interfaces the dose volume goals 154 into a progressive optimization algorithm as the initial starting point rather than a fixed template of goals. Typically, a progressive algorithm uses a fixed template as an initial starting point and then creates a patient specific plan after a significant number of iterations. In the present application, the auto-planning module 36 interfaces the matched plan, specifically the DVH values, from the shape-based algorithm into the progressive algorithm to generate an optimized radiation therapy plan. The progressive algorithm uses the shape-based algorithm output as a patient specific starting point and iteratively operates on the output to generate the optimal treatment plan. The shape-based algorithm output provides a better defined start point for the progressive algorithm that results in reduced iterations of the progressive algorithm and saves processing power and time.

The progressive algorithm progressively refines the set of dose objectives from the shape-based algorithm to drive an inverse planning optimization towards the optimal solution in a complex multi-dimensional space. The optimal treatment plan is typically stored in a treatment plan memory 20 of the therapy system 10.

With continuing reference to FIG. 2, the progressive algorithm includes inverse planning optimization 156 to generate a treatment plan. The inverse planning optimization routine can be any number of well-known routines. The goal is to reduce the dose to the critical structures and other non-target structures to a point just before significant coverage of the target structures is compromised, while maintaining intended dose coverage of the target structures.

The inverse planning optimization routine includes determining a tuning force for each of the dose objectives. The tuning force is based on one or more of the dose, the weight, the current value (i.e., an objective assessment against the optimizer's solution), and any number of biological parameters, such as "a" value. If the tuning force corresponds to a critical structure, the tuning force pushes the dose of the corresponding region towards a lower level. However, if the tuning force corresponds to a target structure, the tuning force pushes the dose of the corresponding region towards the dose profile of the target structure. A determination is then made as to whether the clinical goals are met based on the comparison. For example, insofar as the similarity between the treatment plan and the clinical goals exceeds a predetermined level, the treatment plan represents the optimal treatment plan. Otherwise, the dose objectives are reformulated.

After the treatment plan is generated, the treatment plan is compared 158 to the clinical goals, such as the dose profiles of the structures or heterogeneity indexes, to quantitatively assess how well the treatment plan achieves the clinical goals. The comparison and quantitative assessment can, for example, be performed by a scoring routine designed to score how well the treatment plan achieves the clinical goals. The clinical goals are incorporated into, or otherwise defined by, the planning parameters. A determination 160 is then made as to whether the clinical goals are met based on the comparison 158. For example, insofar as the similarity between the treatment plan and the clinical goals exceeds a predetermined level, the treatment plan represents the optimal treatment plan. Otherwise, the dose objectives are reformulated 162.

Reformulating the dose objectives guides towards an optimal solution (as per the user priority) by driving the tuning forces while maintaining a state of equilibrium. If a critical structure does not meet a clinical goal, the tuning force of the corresponding dose objective is adjusted towards a lower dose or weight. Otherwise, the tuning force is adjusted based on the priority of the critical structure and clinical guideline requirements to achieve the optimal trade-off.

To reformulate the dose objectives, the current value of each of the objective functions is determined. As noted above, the current value is an objective assessment against the optimizer's solution (i.e., the treatment plan). The current value is compared to a predetermined convergence value, for example, specified by the user using the user input device. If the current value is less than the predetermined convergence value, the parameters of the dose objective are modified to increase the current value of the dose objective to approximately the predetermined convergence value. If the current value is greater than the predetermined convergence value, the parameters of the dose objective are modified to decrease the current value of the dose objective to approximately the predetermined convergence value.

In addition to modifying the parameters of the dose objectives, additional dose objectives can be added for high priority structures and/or the weights of existing objectives can be adjusted. For example, an objective can be added to achieve the corresponding clinical goal but not push beyond the goal. As another example, hot and/or cold spots can be identified and objectives corresponding to these spots can be added to achieve a conformal dose distribution to target structures. As another example, dose spillage outside of target structures can be identified and objectives can be added to reduce the identified spillage.

In some embodiments, the optimal treatment plan generated by progressive algorithm does not meet every goal and objective as set forth from the shape-based algorithm. A trade-off module 40 generates alternate trade-off plans 164 using clinical goals and the optimized treatment plan from the auto-planning module 36. The trade-off module 40 receives the candidate treatment plan from the auto-planning module 36. The trade-off module 40 evaluates the candidate treatment plan against the input clinical objectives and determines if the objectives are satisfied. If the objectives are satisfied, the optimized treatment plan is selected without the trade-off module 40 generating alternate trade-off plans.

If the objectives are not satisfied, alternative plans are generated to show the results if each objective or combination of objectives are met. The candidate plan is compared to the DVH and/or other dose information retrieved from the knowledge base by the trade-off module 40. Statistics about all similar knowledge in the database is also used. If the dose sparing achieved by the plan for an OAR is worse (or statistically significantly worse) than the dose predicted by the shape based algorithm, that OAR is a candidate for trade-off analysis. An alternative plan that achieves the predicted dose is presented. If the current plan improves upon the current knowledge, the knowledge base (or model) is improved and the baseline becomes stricter. In addition, trade-off plans can also be generated for select treatment goals that are not met as defined in detail below.

If the trade-off module 40 determines the treatment plan does not meet all the clinical objectives, then a trade-off analysis is performed. The user reviews the trade-off determinations made by the trade-off module 40. In one embodiment, the trade-off module 40 controls the auto-planning module 36 to generate an alternate treatment plan with the unmet objectives constrained to be met or met more fully. In another embodiment, the trade-off module displays the determinations where goals are met or not met to the user on the display. The user uses the user input to explore alternate treatment plans further via a trade-off analysis. In another embodiment, the organs-at-risk are automatically selected by the trade-off module 40.

The user has the option to input priority rankings for specific objectives. In one embodiment, the priority rankings are categorized, i.e. low, medium, and high. In another embodiment, the priority rankings are relative numeric values, i.e. 1-10. The user can select the objectives and the priorities through the user input 32 and the auto-planning module 36 attempts to satisfy the higher priority goals at the expense of lower priority goals. In one embodiment, the trade-off module 40 strives to meet the unmet objectives significantly above others to show how the candidate treatment plan changes. In one embodiment, the priorities and selected organs-at-risk are selected to a predetermined plan template.

In one embodiment, the trade-off module 40 performs trade-off analysis by generating at least one alternate plan using the already generated treatment plan as a starting point. Using the generated plan saves time and effort in recreating plans from the beginning. In one embodiment, the trade-off module 40 copies the original generated plan for each organ-at-risk or other goal that is not met or selected. The trade-off module 40 drives the optimization algorithm to meet, or more closely meet, the unmet goals by changing the optimization parameters for the specific organ-at-risk. Once the goals are met for the specific organ-at-risk, the trade-off module 40 attempts to meet the rest of the goals for the remaining organs-at-risk. In one embodiment, the trade-off module 40 attempts to meet the remaining goals while optimizing to meet the goals for the specific organ-at-risk. The trade-off module 40 creates a plurality of alternate trade-off plans corresponding to each unmet goal for each selected organ-at-risk. The generated trade-off plans show the effect of meeting one of the goals on the rest of the goals for the target and organ-at-risk structures. In one embodiment, trade-off plans are generated for a combination of unmet organ-at-risk goals.

After the trade-off plans are generated, the trade-off module 40 performs further trade-off analysis for comparing plans to each other. The user uses plan comparison features such as DVH overlap or side by side trial dose to evaluate the trade-offs in the trade-off plans. In one embodiment, dose estimates for plans are created by interpolating between two dose grids using a mixing parameter to control the level of interpolation.

In one embodiment, the user selects from one of the alternate trade-off plans or the candidate plans to be delivered to the patient. In another embodiment, the final plan is selected automatically by the trade-off module 40. After the plan is selected, the trade-off module 40 optionally updates the machine learning database 38 with the selected plan for use in future IMRT planning. For example, the selected plan stored in the database can be used as an already generated trade-off plan in the future when the objectives for an organ-at-risk are not met.

A delivery system 42 executes the selected treatment plan to deliver therapy, such as ablation therapy, external beam radiation therapy and/or brachytherapy, to the patient. The therapy typically includes radiation, such as one or more of x-rays, protons, high-intensity focused ultrasound (HIFU), and the like. The delivery system 42 includes a delivery apparatus 44, such as a linear particle accelerator, and a control system 46, which controls the delivery apparatus 44 in accordance with the optimal treatment plan. The optimal treatment plan is typically received from the treatment plan memory 20, but other sources are contemplated.

It is appreciated that a user may exercise increased control of the automatic plan generation by confirming automatically determined selections after some or all of the steps. As used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet/Intranet server from which the stored instructions may be retrieved via the Internet/Intranet or a local area network; or so forth. Further, as used herein, a processor includes one or more of a microprocessor, a microcontroller, a graphic processing unit (GPU), an application-specific integrated circuit (ASIC), a field programmable gate array (FPGA), and the like; a controller includes: (1) a processor and a memory, the processor executing computer executable instructions on the memory embodying the functionality of the controller; or (2) analog and/or digital hardware; a user input device includes one or more of a mouse, a keyboard, a touch screen display, one or more buttons, one or more switches, one or more toggles, voice recognition engines, and the like; a database includes one or more memories; and a display device includes one or more of a liquid crystal display (LCD), a light emitting diode (LED) display, a plasma display, a projection display, a touch screen display, and the like.

Although the system and method of the present disclosure have been described with reference to exemplary embodiments thereof, the present disclosure is not limited to such exemplary embodiments. Rather, the system and method disclosed herein are susceptible to a variety of modifications, enhancements and/or variations, without departing from the spirit or scope hereof. Accordingly, the present disclosure embodies and encompasses such modifications, enhancements and/or variations within the scope of the claims appended hereto.

The invention claimed is:

1. A therapy planning system for generating an optimal treatment plan, said system comprising:
   at least one processor programmed to:
      receive a plurality of treatment plan objectives;
      receive diagnostic imaging data of a subject;
      capture geometries of organs at risk and a target volume specific to the subject;
      access a knowledgebase and match the captured geometries to a previously generated treatment plan returned from the knowledgebase using proximity information, overlap and a calculated shape metric;
      optimize a plurality of treatment plan parameters based on the plurality of objectives to generate a treatment plan;
      reformulate the plurality of objectives including at least one of modifying parameters of the plurality of objectives and adding one or more additional objectives to the plurality of objectives;
      repeat the optimizing based on the reformulated plurality of objectives to generate a reformulated treatment plan;
   wherein the at least one processor is further programmed to:
      construct subject specific dosimetric information from the previously generated treatment plan; and
      interface the dosimetric information as initial subject specific treatment plan objectives for optimization.

2. The system according to claim 1,
   wherein the interfacing includes calculating inflection points of a DVH curve(s) and deriving the dosimetric information from the calculated inflection points.

3. The system according to claim 1, wherein the reformulating and the optimizing are repeated for a predetermined number of iterations or until the clinical goals are met.

4. The system according to claim 1, wherein the optimizing includes:
   determining a tuning force for each objective, the tuning force based on one or more of a dose, a weight and a current value, the current value assessing the extent to which a current solution achieves the objective; and,
   adjusting dose to regions corresponding to the plurality of structures, wherein tuning forces corresponding to critical structures push towards lower doses while tuning forces corresponding to target structures simultaneously push towards uniform or higher doses.

5. The system according to claim 1, comprising:
   a planning image memory which stores a volume diagnostic image;
   a memory for storing clinical objectives configured for a user to input data defining organs-at-risk and clinical goals regarding target radiation dose delivered to a target and organs-at-risk; and
   the at least one processor configured to:
      evaluate the treatment plan by comparing the target radiation dose to the dose delivered to each of the organs-at-risk by the first treatment plan;
      generate one or more additional subsequent treatment plans constraining the clinical goals to bring a difference between the target and delivered radiation dose closer for at least one of the organs-at-risk; and
      display the first and one or more subsequent treatment plans to a user to select a final plan from the first and at least one subsequent treatment plans.

6. The system according to claim 1, wherein the processor is further configured to:
   receive a priority ranking for the target radiation dose delivered to each of the organs-at-risk; and
   generate the at least one subsequent treatment plan adjusting the priority rankings.

7. The system according to claim 1, wherein the at least one processor is further programmed to store a final plan in the knowledgebase.

8. The system according to claim 1, wherein the at least one processor further programmed to:
   generate trade-off treatment plans to meet user-selected prioritized goals;
   select a final plan as at least one of a plurality of optimized treatment plans and one of the generated trade-off treatment plans.

9. A method for generating an optimal treatment plan, comprising:
  receiving a plurality of treatment plan objectives;
  receiving diagnostic imaging data of a subject capturing geometries of organs at risk and a target volume specific to the subject;
  accessing a knowledgebase and matching the captured geometries to a previously generated treatment plan returned from the knowledgebase using proximity information, overlap and a calculated shape metric,
  optimizing a plurality of treatment plan parameters based on the plurality of objectives to generate a first treatment plan;
  reformulating the plurality of objectives including at least one of modifying parameters of the plurality of objectives and adding one or more additional objectives to the plurality of objectives;
  repeating the optimizing based on the reformulated plurality of objectives to generate a reformulated treatment plan;
  wherein
  constructing subject specific dosimetric information from the previously generated treatment plan; and
  interfacing the dosimetric information as initial subject specific treatment plan objectives for optimization.

10. The method according to claim 9:
  wherein the interfacing includes calculating inflection points of a DVH curve and deriving the dosimetric information from the calculated inflection points.

11. The method according to claim 9, wherein the reformulating and the optimizing are repeated for a predetermined number of iterations or until at least one clinical goal is met.

12. The method according to claim 9, wherein wherein the optimizing includes:
  determining a tuning force for each objective, the tuning force based on one or more of a dose, a weight and a current value, the current value assessing the extent to which a current solution achieves the objective; and
  adjusting dose to regions corresponding to a plurality of structures, wherein tuning forces corresponding to critical structures push towards lower doses while tuning forces corresponding to target structures simultaneously push towards higher doses.

13. The method according to claim 9, further including:
  evaluating a subsequent treatment plan by comparing the target radiation dose to a dose delivered to each of the organs-at-risk by the first treatment plan;
  generating one or more additional subsequent treatment plans constraining the clinical goals to bring a difference between the target and delivered radiation dose closer for at least one of the organs-at-risk;
  displaying the first and one or more subsequent treatment plans to a user to select a final plan from the first and at least one subsequent treatment plans.

14. The method according to claim 9, further including:
  receiving a priority ranking for a target radiation dose delivered to each of the organs-at-risk; and
  generating the at least one reformulated treatment plan adjusting the priority rankings.

15. A non-transitory computer readable medium carrying software for controlling one or more processors to perform the method of claim 9.

* * * * *